Figure 1:
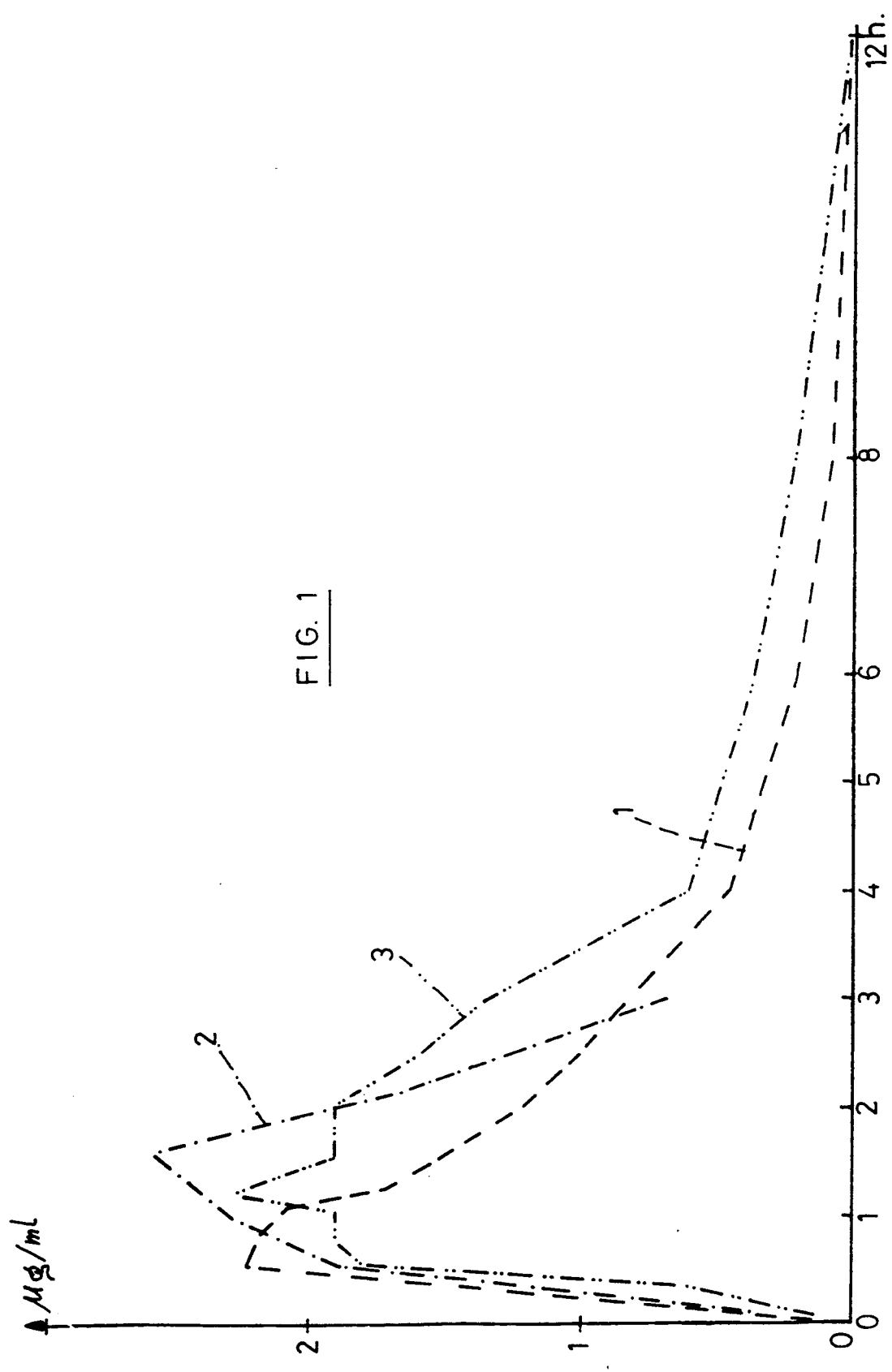

United States Patent [19]

Rossignol

[11] Patent Number: 5,118,799
[45] Date of Patent: Jun. 2, 1992

[54] PROCESS FOR CONVERTING CRYSTALLINE ERYTHROMYCIN ETHYLSUCCINATE INTO STABLE AMORPHOUS ERYTHROMYCIN ETHYLSUCCINATE

[75] Inventor: Jean F. Rossignol, Philadelphia, Pa.

[73] Assignee: Pharmacin Corporation, St. Petersburg, Fla.

[21] Appl. No.: 428,008

[22] Filed: Oct. 27, 1989

Related U.S. Application Data

[63] Continuation of Ser. No. 48,698, May 12, 1987, abandoned.

[51] Int. Cl.⁵ .............................................. C07H 1/00
[52] U.S. Cl. ................................... 536/7.2; 536/18.5
[58] Field of Search ..................... 536/7.2, 7.4, 18.5; 514/29

[56] References Cited

U.S. PATENT DOCUMENTS

| | | | |
|---|---|---|---|
| 2,653,899 | 9/1953 | Bunch et al. | 536/7.2 |
| 3,878,192 | 4/1975 | Blasina et al. | 536/7.2 |
| 4,076,804 | 2/1978 | Singiser et al. | 514/29 |
| 4,127,647 | 11/1978 | Sato et al. | 514/29 |
| 4,132,781 | 1/1979 | Stoughton | 514/29 |

*Primary Examiner*—John W. Rollins
*Assistant Examiner*—Elli Peselev
*Attorney, Agent, or Firm*—Sughrue, Mion, Zinn, Macpeak & Seas

[57] ABSTRACT

This invention relates to a process for converting crystalline erythromycin ethylsuccinate into stable amorphous erythromycin ethylsuccinate, and to the use of this stable amorphous ethylsuccinate in pharmaceutical compositions which may possibly contain pharmacologically acceptable excipients, surfactants and the like.

3 Claims, 3 Drawing Sheets

X-RAY DIFFRACTION SPECTRUM OF CRYSTALLINE ERYTHROMYCIN ETHYLSUCCINATE

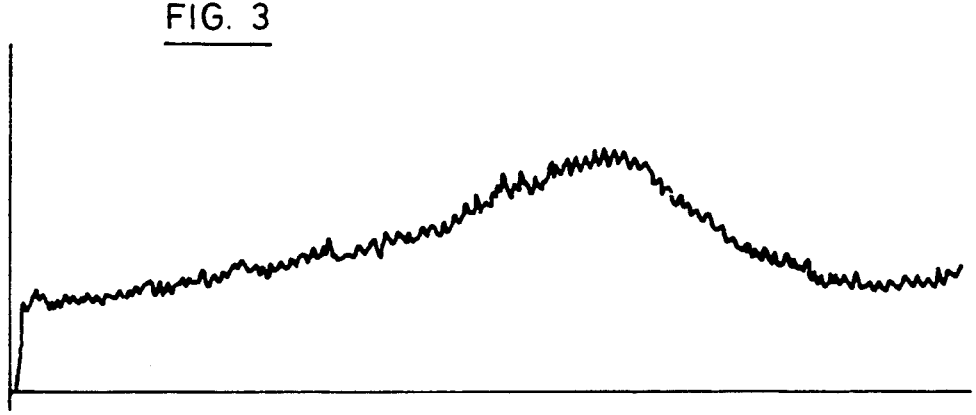
X-RAY DIFFRACTION SPECTRUM OF AMORPHOUS ERYTHROMYCIN ETHYLSUCCINATE AFTER 20 MONTHS OF CONSERVATION.
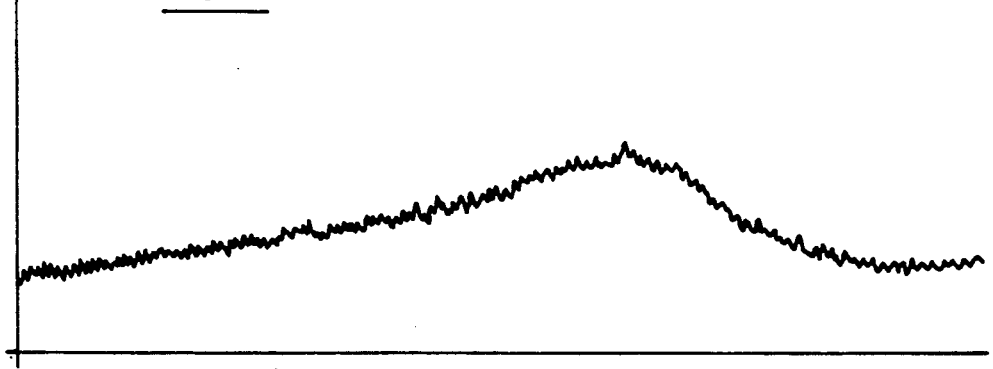
X-RAY DIFFRACTION SPECTRUM OF AMORPHOUS ERYTHROMYCIN ETHYLSUCCINATE AFTER PREPARATION

PROCESS FOR CONVERTING CRYSTALLINE ERYTHROMYCIN ETHYLSUCCINATE INTO STABLE AMORPHOUS ERYTHROMYCIN ETHYLSUCCINATE

This is a continuation of application Ser. No. 048,698, filed May 12, 1987, now abandoned.

PRIOR ART

Macrolides such as erythromycin and erythromycin derivatives are extremely useful antibiotics active against gram positive bacteria and some gram negative organisms. Erythromycin is a drug used for patients who are allergic to penicillins.

Erythromycin is used in the treatment of chlamydial infections and legionnaires disease and has never produced significant side effects or toxicity It is known to use stable crystalline erythromycin ethylsuccinate or other drugs belonging to the macrolides. In fact, amorphous products are more soluble and therefore better absorbed in humans. However, products which do not precipitate in the amorphous state are metastable; this means that these products tend to return to the stable crystalline state within a few days or weeks.

For example, the antibiotic novobiocin is very soluble but not stable in the amorphous state, so that this antibiotic returns into its stable crystalline state, this crystalline state being poorly soluble and absorbed.

It is also known from French patent application no. 82-06646 that amorphous hydroflumethiazine or dipyridamole returns to crystalline state within 12 days and from French patent 76-10280 that amorphous macrolides are very unstable; for example acetyl-9 acetyl-3" midecamycin and josamycin return to their stable crystalline state within 2 weeks and kitazamycin returns partially to its crystalline state within 1 month and totally thereafter.

It is also known, according to French patent no. 80 14827, to produce slow-release formulations of active drugs containing amorphous products. The amorphous active drugs are stabilized by means of cellulose derivatives which are melted with the active drug during its preparation in the amorphous state. Such stabilizing agents are, for example, hydroxypropylmethylcellulose, methylcellulose or polyvinylpyrrolidone.

French patent 76-10280 and French patent application 82-06646 show that it is possible to stabilize immediately released formulations containing amorphous drugs by adding to these drugs stabilizing agents or crystal-preventing agents, such as ethylcellulose, hydroxymethylcellulose, hydroxypropylmethylcellulose, hydroxypropylcellulose phtalate, polyvinylpyrrolidone possibly mixed with polyethyleneglycol.

But whether or not a stabilizing agent is added, drugs in a stable crystalline state cannot be easily converted into amorphous solids having an acceptable stability.

Under these circumstances, such formulations are not commercially available except, of course, those being normally stable in the amorphous state.

BRIEF DESCRIPTION OF THE INVENTION

The present invention relates to a process for converting crystalline erythromycin ethylsuccinate into stable amorphous erythromycin ethylsuccinate and to the use of this stable amorphous erythromycin ethylsuccinate, as active ingredient, in pharmaceutical compositions.

For converting crystalline erythromycin ethylsuccinate into a stable amorphous product, the crystalline erythromycin ethylsuccinate is melted at about 110° C. either in an oven with a circulating ventilation or with a thermoregulated oil bath. The melted product is kept in the melted state for 1 or 2 minutes. It is then left at room temperature and it resolidifies as amorphous solid. It is then ground with a classical grinder into a fine white powder.

Other macrolides, such as erythromycin base, erythromycin stearate or josamycin, are partially degradated during the process, the stearate being in addition hydrolysed as shown by the microbiological titers and the HPLC spectra. In fact the melting of erythromycin base has been described in the French Patent Application No. 1,559,631 as being a method to produce another polymorph of crystalline erythromycin base with a melting point of 183°-190° C. instead of 135°-140° C. for the pharmaceutically used product. In any case it does not produce an amorphous erythromycin base.

The invention is based on the discovery that an amorphous erythromycin ethylsuccinate has a stability similar to that of crystalline erythromycin ethylsuccinate.

The amorphous character of the erythromycin ethylsuccinate obtained by the process according to this invention has been demonstrated by a X-ray diffraction spectrum which clearly shows a strong diffusion extending all over the spectrum, two distinct halos at $\theta = 5°$ and $11°$ and a third vague halo at about $\Gamma = 18°$, i.e. at $k = 0.612$ Å$^{-1}$, $1.34$ Å$^{-1}$ and $2.2$ Å$^{-1}$. The spectrum has been determined by placing powdered amorphous erythromycin ethylsuccinate in Lindeman capillary tubes which were placed in a D.S. chamber with a diameter of 114.6 mm and under a CoK$_\alpha$ ($\lambda = 1.789$ Å) radiation.

The invention relates also to pharmaceutical compositions for oral administration containing amorphous stable erythromycin ethylsuccinate as active ingredient possibly together with at least one pharmaceutically acceptable carrier or excipient.

Suitable excipients are, for example, starch, kaolin, calcium phosphate, talc, calcium carbonate, lactose, saccharose carboxymethylcellulose, sodium alginate, methylcellulose, dextrin, glucose and the like.

The pharmaceutical compositions according to this invention may comprise, by weight, from 0.1% to 90% of stable amorphous erythromycin ethylsuccinate and from 99.9% to 10% of excipients.

Besides the foregoing excipients, the compositions according to the invention may, if necessary, comprise other additives such as binders, lubricants and the like.

The number and type of excipients or other additives used will depend upon the desired dosage unit form. The terms "dosage unit" mean a unitary or single dose which may be administered to a patient and which may be readily handled and packed, remaining as a physically stable dose. This dosage unit may comprise stable amorphous erythromycin ethylsuccinate, possibly in combination with at least one excipient or suitable additive.

The dosage units of pharmaceutical compositions according to the present invention may be in the form of powders or granules in sachets or in capsules or gelules, in tablets, in pills or any other galenic dry formulation which may be orally administered to patients (humans or animals).

The dosage units of pharmaceutical compositions according to the present invention may be administered one or more times a day at predetermined intervals, the length of which will depend on the condition of the patient. A daily dose may contain from about 1 to 10 grams of the pharmaceutical composition.

This pharmaceutical composition may also be in the form of slow release formulations, a form which progressively liberates the active agent into the body by the use, for example, of the known microencapsulation techniques.

This galenic form allows the administration of a single dose per day or at least produces more uniform blood levels over 8 to 10 hours. Also in this case, the dosage form may comprise from 1 gram to 10 grams of the pharmacologically active ingredient.

The conversion of the starting crystalline erythromycin ethylsuccinate into an amorphous product is very easy, as described above.

EXAMPLE

The following example further describes the present invention, but is not to be construed as limiting the invention.

Preparation of a pharmaceutical composition containing erythromycin.

a) Erythromycin ethylsuccinate (lot 1164 supplied by DESHORS—France and analytically conform to the American Pharmacopoeia U.S.P. XXX) was melted in an electric stove at 110° C.

The yellowish molten product was poured after 2 minutes into a porcelain mortar at room temperature where the product became quickly solid in the form of an amorphous mass which was then crushed so as to obtain an amorphous powder of fine particles. The analysis of a sample of this powder confirmed that it was conform to the American Pharmacopoeia (microbiological titre, HPLC, IR, UV, RMN and X ray diffraction spectra).

The crystalline erythromycin ethylsuccinate has a melting point of 110° C. The same product, in amorphous form, melts at 165° C.

b) 710 grams of powder of amorphous erythromycin ethylsuccinate, which was obtained as described hereabove, were used for producing microgranules soluble in water, according to the following formula:

| | |
|---|---|
| Amorphous erythromycin ethylsuccinate | 710.00 grams |
| Saccharose distearate (Sucro ester 15) | 23.15 grams |
| Sodium citrate | 658.84 grams |
| Saccharin (sodium salt) | 19.76 grams |
| Sherry flavoring agent (Selva 3352) | 49.41 grams |
| Silica (Aerosil 200) | 94.43 grams |
| Sodium laurylsulfate | 62.60 grams |
| Erythrosine (dye) | 1.72 grams |
| Sugar | 93.00 grams |
| Demineralized water | 250.00 grams |

In order to obtain these microgranules, known excipients and a classical mode of operation were used. More precisely, granules were first prepared using a classical technique, by means of all the ingredients, except the amorphous erythromycin ethylsuccinate and the sucro ester. After drying and calibration, the granules were mixed with the erythromycin ethylsuccinate and the sucro ester in a Rhön wheel during 15 minutes.

The mixture was finally distributed in sachets, each containing the equivalent of 500 mg of erythromycin base.

The invention relates also to the use of amorphous erythromycin ethylsuccinate for preparing pharmaceutical compositions to be orally administered.

TESTS

The following tests show that the amorphous erythromycin ethylsuccinate is more soluble and better absorbed than crystalline erythromycin ethylsuccinate and that amorphous erythromycin ethylsuccinate remains stable for a long period of time.

Three male volunteers being from 26 to 36 years old and having a weight comprised between 59 and 76 kg were submitted to a medical exam as well as a complete urine and blood biochemical and hematological testing before receiving the erythromycin preparation.

I. Different studies were conducted on the voluntary humans in order to compare the pharmaceutical compositions containing amorphous erythromycin in the form of ethylsuccinate and commercial compositions also containing erythromycin ethylsuccinate.

In comparing the bioavailabilities of these pharmaceutical preparations of similar compositions, but of different origin, two major pharmakocinetic parameters were considered, namely the intensity and speed of the passage of the antibacterial agent into the body of patients to whom these compositions were orally administered.

In the experimental studies of the kind reported herein, bioavailability may generally be correlated to the periodic plasmatic concentrations of the unchanged antibiotic; said concentrations may be determined by titrations.

All these studies were conducted under the supervision of Hervé Maisonneuve, M.D. in the hospital "de la Croix Rousse", Lyon, France and of Jean-Claude Torlotin, Pharm. D., Department of microbiology, Hospital Herold, Paris, France.

After fasting, and at least 7 day intervals, each subject received a unit dose of each compared preparation and blood samples were drawn before the beginning of the treatment and 20,30, 45 and 60 minutes after the beginning of the treatment, and again at 1.15, 1.30, 2.0, 2.30, 3.0, 4.0, 6.0, 8.0 and 12.0 hours after the beginning of the treatment. The blood samples were taken by catheterization of the forearm vein. Once drawn, each blood sample was rapidly centrifuged and decanted, the plasma being then immediately frozen ($-18°$ C.) and kept in this state until the determination of erythromycin content.

The following assay technique was used to determine the erythromycin content of the blood samples with reference sera or serum standards in the presence of a sensitive microbial agent.

The assays were carried out using glass plates (cut or flat glass having parallel sides), which had the size of 250 mm (9.85 inches) by 250 mm (9.85 inches) and on which a sliding scale frame was attached by means of a cellophane adhesive tape, the sliding scale having a size of $250 \times 25 \times 8$ mm ($9.85 \times 0.895 \times 0.315$ inches). The marked surfaces allowed the simultaneous dosage of three samples within a sampling range of 5 points. Each dosage was performed in triplicate. The position of the range and of the samples to be measured was determined at random.

Before their use, the plates were incubated several hours in an oven at 39° C. Before their incubation a 250 mm (9.85 inches)×250 mm (9.85 inches) cover glass was placed on the frame formed by the sliding scales.

The following culture medium was used:

| | |
|---|---|
| Peptone (UCLAF - France) | 3.0 grams |
| Yeast autolysate (BYLA - France) | 4.0 grams |
| Beef extract (LIEBIG) | 1.5 gram |
| Gelose (Agar) | 15 grams |
| Distilled water q.s. ad | 1000 ml |

The pH of this medium was adjusted to 8 after dissolution and portions of this medium were distributed in 50 ml flasks, a thin layer of about 1 mm (0.039 inch) thick being obtainable on plates with this volume.

The culture medium samples were sterilized at 110° C. for 30 minutes.

In view of the low concentrations expected to be found in the blood serum after oral administration of erythromycin, Sarcina lutea was used as bacterial agent because of its extreme sensitivity to this macrolide. The ATCC strain of accession no. 9341 was used as Sarcina lutea strain.

After cultivation in ordinary gelose for 48 hours, the microbial germs were collected in 10 ml of sterile distilled water. The obtained concentrated suspension was maintained in sealed vials for one month at 4° C.

From said suspension, a working suspension having an optical density (O.D.) of 0.25 mm (0.01 inch) to 520 mm (20.47 inches) was prepared by dilution.

The following standard sera and reagents were prepared for titration.

REAGENT 1 mixture of sterilely drawn serum samples from subjects not receiving any antibiotics. After being heated for 30 minutes at 56° C. the mixture was distributed into vials of 5 ml.

REAGENT 2

Buffer solution, pH: 8
$KH_2 PO_4$ 0.34 grams
$Na_2 HPO_4, 12H_2O$ 17.50 grams
Distilled water q.s.ad 1000 ml.

This reagent was distributed into flasks of 50 ml and sterilized for 30 minutes at 110° C.

REAGENT 3 aqueous solution with 80% by volume of isopropanol.

For this reagent 3, a mother solution containing, for example, 1000 mg/l was prepared. This alcoholic solution was kept for 15 days at 4° C.

By dilution in the reagent 2, a working solution of 0.8 mg/l was obtained, said solution being used to prepare the standard series according to the details of the following table:

| TABLE REPRESENTING A STANDARD SERIES OF ERYTHROMYCIN | | | | |
|---|---|---|---|---|
| volumes in ml | | | | |
| Tube n° | 1 | 2 | 3 | 4 |
| 8 mg/l solution | 1 | 1 | 1 | 1 |
| Buffer solution, pH 8 | | 1 | | |
| Serum (reagent 1) | 1 | | 1 | 1 |

| TABLE REPRESENTING A STANDARD SERIES OF ERYTHROMYCIN | | | | |
|---|---|---|---|---|
| volumes in ml | | | | |
| Tube n° | 1 | 2 | 3 | 4 |
| Final concentration (mg/l) | 0.4 | 0.2 | 0.1 | 0.05 |

By convention, the results of the assays have been expressed in terms of erythromycin base.

Samples to be titrated

The samples to be titrated were diluted to a half, to a quarter or to a tenth in the buffer solution of pH 8 (reagent 2).

It should be noted that the hydrolysis of the ethylsuccinate was complete, when the serum sample was kept for one hour at 37° C., before the dosage.

The plates were reheated by placing them for one hour in an incubator at 37° C. The plates equipped with their frame and a gelose water tight seal were arranged on a perfectly horizontal support. For this purpose, a tray resting on three bearings was used.

The horizontal arrangement was verified by means of a spirit level.

The gelose which was liquefied in a water bath at 55° C. received the inoculum at a rate of 2 ml per 100 ml of gelose and a solution of 5% gelose (also 2 ml per 100 ml of gelose).

After carefully mixing, the medium was quickly and totally poured into the middle of the plate, the uniformity of the distribution being obtained by a slight tilting movement.

The plate was then placed on the support and the cover put in place. The medium was then allowed to become solid.

Wells were then cut in the middle of the solidified medium.

The different solutions of the sera to be tested and of the samples were divided into fractions of 20 ml and were allowed to diffuse for 30 minutes first at room temperature and then in the incubator at 30° C. for 24 to 30 hours.

After this period of incubation, the diameters of inhibition of the cultures were measured, either by means of dividers or by projecting the image enlarged 7 times using a microfilm reader. The average of the diameters determined for each dilution was calculated and a standard curve was traced by plotting these average values on a semi-logarithmic coordinate paper. The antibiotic content of the samples was thus determined.

In this first study, the effects of the three following products which were administered in a single dose were compared:

a single 1000 mg oral dose of erythromycin active base as crystalline erythromycin ethylsuccinate granules, i.e. one sachet of Erythrocin 1000. Abbott;

a single 500 mg oral dose of erythromycin active base as crystalline erythromycin ethylsuccinate granules i.e. one sachet of the Erythrocin 500, Abbott;

a single 500 mg oral dose of erythromycin active base as amorphous erythromycin ethylsuccinate according to the invention.

The following table I shows that the concentration of erythromycin base in the serum is greater if the erythromycin is absorbed in an amorphous state. A dose of 500 mg of amorphous erythromycin according to the invention gives about the same result as a dose of 1000 mg of crystalline erythromycin (Erythrocin 1000, Abbott).

TABLE 1

| Times (h) | INDIVIDUAL VALUES IN MCG/ML IN ERYTHROMYCIN BASE | | | | | | | | | | | |
|---|---|---|---|---|---|---|---|---|---|---|---|---|
| | Erythrocin 1000 Abbott Subject No | | | | Erythrocin 500 Abbott Subject No | | | | Amorphous erythromycin ethylsuccinate Subject No | | | |
| | 1 | 2 | 3 | Mean | 1 | 2 | 3 | Mean | 1 | 2 | 3 | Mean |
| 0.00 | 0.00 | 0.00 | 0.00 | 0.00 | 0.00 | 0.00 | 0.00 | 0.00 | 0.00 | 0.00 | 0.00 | 0.00 |
| 0.33 | 0.80 | 2.00 | 2.50 | 1.76 | 0.00 | 0.00 | 0.00 | 0.00 | 0.50 | 2.20 | 2.00 | 1.56 |
| 0.50 | 1.40 | 2.80 | 3.20 | 2.46 | 0.15 | 0.05 | 0.00 | 0.06 | 0.90 | 2.80 | 3.00 | 2.23 |
| 0.75 | 1.50 | 3.00 | 3.00 | 2.50 | 0.30 | 0.10 | 0.50 | 0.30 | 0.90 | 2.80 | 2.90 | 2.20 |
| 1.00 | 1.50 | 2.80 | 3.00 | 2.43 | 0.50 | 0.15 | 0.80 | 0.48 | 0.80 | 2.70 | 2.80 | 2.10 |
| 1.25 | 1.50 | 2.20 | 2.30 | 2.00 | 0.45 | 1.00 | 1.00 | 0.81 | 0.70 | 2.20 | 2.20 | 1.70 |
| 1.50 | 1.40 | 2.00 | 2.00 | 1.80 | 0.40 | 1.30 | 1.00 | 0.90 | 0.60 | 2.00 | 2.00 | 1.53 |
| 2.00 | 1.30 | 1.80 | 1.30 | 1.46 | 0.35 | 1.80 | 1.00 | 1.05 | 0.50 | 1.50 | 1.60 | 1.20 |
| 2.30 | 1.10 | 1.50 | 1.10 | 1.23 | 0.30 | 1.50 | 0.90 | 0.90 | 0.40 | 1.00 | 1.20 | 0.90 |
| 3.00 | 1.00 | 1.00 | 0.90 | 0.96 | 0.25 | 1.00 | 0.80 | 0.68 | 0.30 | 0.90 | 1.00 | 0.80 |
| 4.00 | 0.60 | 0.60 | 0.50 | 0.56 | 0.15 | 0.50 | 0.45 | 0.36 | 0.20 | 0.50 | 0.60 | 0.43 |
| 6.00 | 0.20 | 0.20 | 0.25 | 0.21 | 0.05 | 0.15 | 0.15 | 0.11 | 0.10 | 0.18 | 0.25 | 0.20 |
| 8.00 | 0.08 | 0.08 | 0.09 | 0.08 | 0.00 | 0.05 | 0.05 | 0.03 | 0.05 | 0.06 | 0.10 | 0.07 |
| 12.00 | 0.05 | 0.00 | 0.00 | 0.01 | 0.05 | 0.05 | 0.00 | 0.03 | 0.05 | 0.05 | 0.00 | 0.03 |

This table shows that amorphous erythromycin is more soluble and therefore better absorbed in humans than crystalline erythromycin (Erythrocin 500 or 1000).

The following table 2 shows the concentration of erythromycin base in the serum when patients absorbed amorphous erythromycin ethylsuccinate after 15 and 18 months from the manufacture of this product.

TABLE 2

| Times (h) | INDIVIDUAL VALUES IN MCG/ML IN ERYTHROMYCIN BASE | | | | | | | |
|---|---|---|---|---|---|---|---|---|
| | Amorphous erythromycin ethylsuccinate (dose 500 mg) 15 months Subject No | | | | Amorphous erythromycin ethylsuccinate (dose 500 mg) 18 months Subject No | | | |
| | 1 | 2 | 3 | Mean | 1 | 2 | 3 | Mean |
| 0.00 | 0.00 | 0.00 | 0.00 | 0.00 | 0.00 | 0.00 | 0.00 | 0.00 |
| 0.33 | — | — | — | — | 0.60 | 0.80 | 0.50 | 0.63 |
| 0.50 | 1.60 | 2.00 | 2.00 | 1.90 | 2.00 | 2.00 | 1.40 | 1.80 |
| 0.75 | — | — | — | — | 2.10 | 2.40 | 1.20 | 1.90 |
| 1.00 | 2.00 | 1.80 | 3.20 | 2.30 | 2.40 | 2.40 | 1.00 | 1.90 |
| 1.25 | — | — | — | — | 2.40 | 2.20 | — | 2.30 |
| 1.50 | 2.40 | 3.20 | 2.00 | 2.50 | 2.40 | 2.00 | 1.40 | 1.90 |
| 2.00 | 1.60 | 1.80 | 1.60 | 1.70 | 2.00 | 1.80 | 2.00 | 1.90 |
| 2.30 | — | — | — | — | 1.60 | 1.60 | 1.60 | 1.60 |
| 3.00 | 0.80 | 0.50 | 0.80 | 0.70 | 1.30 | 1.40 | 1.30 | 1.33 |
| 4.00 | — | — | — | — | 0.60 | 0.70 | 0.50 | 0.60 |
| 6.00 | — | — | — | — | 0.30 | 0.50 | 0.30 | 0.36 |
| 8.00 | — | — | — | — | 0.20 | 0.22 | 0.18 | 0.20 |
| 12.00 | — | — | — | — | 0.05 | 0.05 | 0.05 | 0.05 |

Attached FIG. 1 shows the blood concentration of erythromycin provided from amorphous erythromycin ethylsuccinate just produced and produced 15 and 18 months ago, in function of the time after the absorption. This FIG. 1 shows clearly that there is substantially no loss of activity of the amorphous erythromycin ethylsuccinate, since the concentration of erythromycin in the serum is about the same with amorphous erythromycin ethylsuccinate just produced and amorphous erythromycin ethylsuccinate produced 15 and 18 months earlier. Thus this figure shows that amorphous erythromycin ethylsuccinate is stable, while according to the prior art the amorphous macrolides were considered as unstable, since they return to the crystalline state.

In said FIG. 1, curves 1, 2 and 3 give the concentrations of amorphous erythromycin ethylsuccinate produced respectively just before, 15 months before and 18 months before the oral administration of 500 mg of said amorphous product to the patients.

Figure 2:
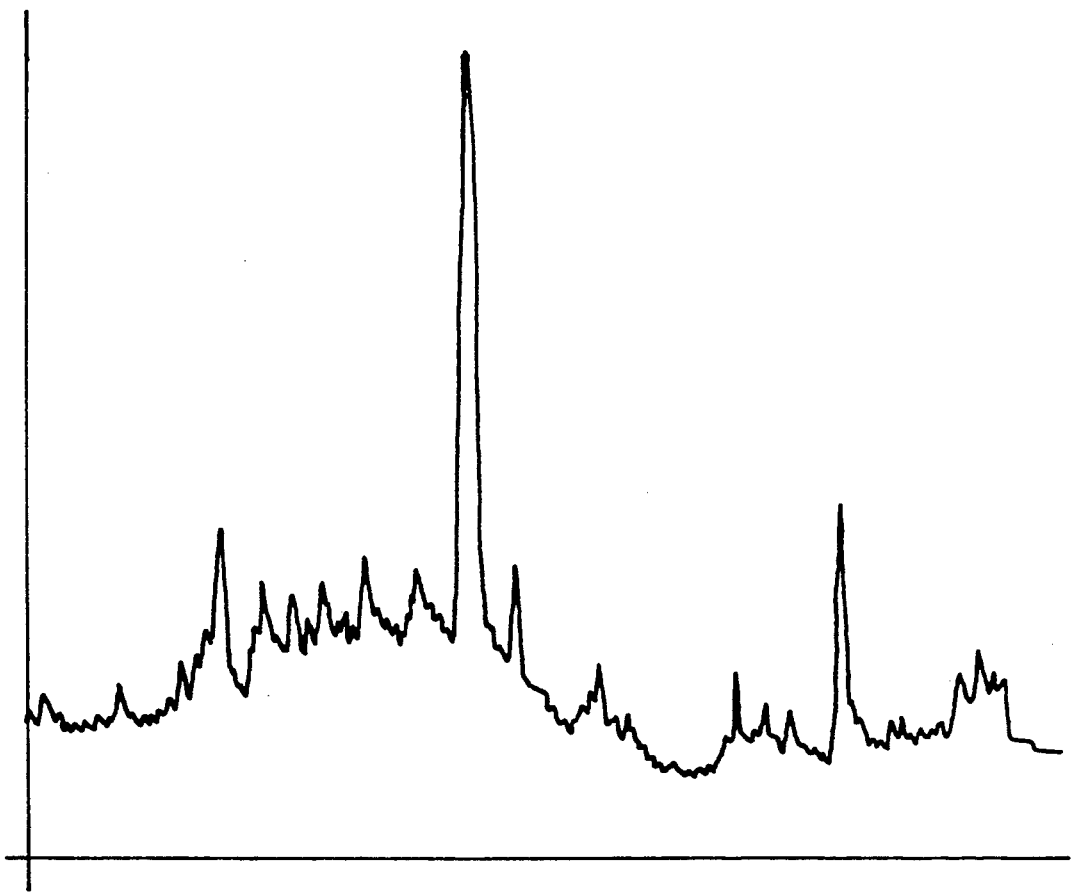

Attached FIG. 2 shows the X-ray diffraction spectrum of crystalline erythromycin ethylsuccinate.

FIGS. 3 and 4 show the X-ray diffraction spectrum of amorphous erythromycin ethylsuccinate respectively after 20 months of conversation and immediately after preparation.

A comparison of the spectra of FIGS. 3 and 4 shows the stability of the amorphous erythomycin ethylsuccinate.

What I claim is:

1. A process for converting crystalline erythromycin ethylsuccinate in conformance to the U.S. Pharmacopeia, in which crystalline erythromycin ethylsuccinate is melted at a temperature of about 100° C. before being cooled, so as to obtain a stable amorphous erythromycin ethylsuccinate in conformance to the U.S. Pharmacopeia, having a microbiological titre which is identical to the crystalline erythromycin ethylsuccinate titre.

2. A process according to claim 1, in which the melted erythromycin ethylsuccinate is kept in a melted phase during about 1 to 2 minutes.

3. A process for converting crystalline erythromycin ethylsuccinate in conformance to the U.S. Pharmacopeia, in which crystalline erythromycin ethylsuccinate is melted at a temperature of about 110° C. before being cooled and ground, so as to obtain a stable amorphous erythromycin ethylsuccinate in conformance to the U.S. Pharmacopeia, having a microbiological titre which is identical to the crystalline erythromycin ethylsuccinate titre.

* * * * *